United States Patent [19]

Alexander et al.

[11] Patent Number: 4,835,138
[45] Date of Patent: May 30, 1989

[54] CHOLINE ESTERS AS ABSORPTION-ENHANCING AGENTS FOR DRUG DELIVERY THROUGH MUCOUS MEMBRANES OF THE NASAL, BUCCAL, SUBLINGUAL AND VAGINAL CAVITIES

[75] Inventors: Jose Alexander; A. J. Repta; Joseph A. Fix, all of Lawrence, Kans.

[73] Assignee: Merck & Co., Inc., Rahway, N.J.

[21] Appl. No.: 50,643

[22] Filed: May 18, 1987

Related U.S. Application Data

[62] Division of Ser. No. 766,377, Aug. 16, 1985, Pat. No. 4,692,441.

[51] Int. Cl.$^4$ .................... A61K 37/26; A61K 37/00; A61K 31/195
[52] U.S. Cl. .......................................... 514/3; 514/11; 514/12; 514/15; 514/561; 514/565; 514/567; 514/946; 514/947
[58] Field of Search ................ 514/946, 947, 3, 11, 514/12, 15, 561, 565, 567

[56] References Cited

U.S. PATENT DOCUMENTS 4,425,337  1/1984  Alexander et al. ................ 424/181
4,462,991  7/1984  Alexander et al. ................ 424/181

Primary Examiner—Frederick E. Waddell
Attorney, Agent, or Firm—Manfred Polk; Michael C. Sudol

[57] ABSTRACT

Choline esters are used as drug absorption enhancing agents for drugs which are poorly absorbed from the nasal, oral, and vaginal cavities.

15 Claims, No Drawings

CHOLINE ESTERS AS ABSORPTION-ENHANCING AGENTS FOR DRUG DELIVERY THROUGH MUCOUS MEMBRANES OF THE NASAL, BUCCAL, SUBLINGUAL AND VAGINAL CAVITIES

CROSS REFERENCE TO RELATED APPLICATIONS

This is a divisional application of U.S. Ser. No. 766,377, filed Aug. 16, 1985, now issued to U.S. Pat. No. 4,692,411.

BACKGROUND OF THE INVENTION

The invention relates to a novel method and compositions for enhancing absorption of drugs from the nasal, buccal, sublingual and vaginal cavities by incorporating therein a choline ester adsorption enhancing agent. The use of choline esters to promote nasal, buccal, sublingual and vaginal drug delivery offers several advantages over attempts to increase drug absorption from the gastrointestinal tract. Drugs are not exposed to the enzymatic activity of the stomach and small intestine, and are not exposed to the acidic environment of the stomach. This can offer significant advantages in drug stability.

DESCRIPTION OF THE PRIOR ART

Though the gastrointestinal tract is the preferred route for drug delivery, all drugs are not well absorbed from this site. In many cases, this may be due to the polar nature or hydrophilic character of these drugs. Since they are precluded from rapid absorption, such drugs are subject to long residency time in the gastrointestinal environment where both acidic and enzymatic degradation contribute to their poor bioavailability. It is, therefore, clear that any factor which enhances the rate of absorption will demonstrate improved clinical efficacy. Considerable effort has been directed in the recent years toward identifying agents which increase gastrointestinal absorption of poorly absorbed compounds. Surface active agents (George, Sutter, Finegold, J. Infect. Dis. 136, 822 (1977), chelating agents (Cassidy, Tidball, J. Cell Biol. 32, 672 (1967), salicylates (Higuchi, et al., U.S. Pat. No. 4,462,991 (1984)), anti-inflammatory agents (Yaginuma et al., Chem. Pharm. Bull. 29, 1974 (1981), phenothiazines (Alexander and Fix, U.S. Pat. No. 4,425,337 (1984) and acyl carnitines (Alexander and Fix, U.S. Ser. No. 606,054) have been shown to increase gastrointestinal permeability to a variety of compounds.

The present use of choline esters to promote absorption from the nasal, buccal, sublingual and vaginal cavities affords several advantages over the prior art's non-related absorption promoting compounds. The choline esters, especially those with medium and long chain fatty acid components, are more potent than the presently used absorption promoting agents. As an example, in aqueous solutions, the choline esters are effective absorption promoting agents at levels as low as 0.05%. By contrast, the effective dose of other known absorption promoters is significantly higher: sodium salicylate—1%, surfactants—1%, chelating agents—2%. This difference in potency affords opportunities for reducing the required size of the dosage form and potentially minimizing side effects. The choline esters cause reversible changes in mucosal cell permeability to the target drug, indicating that a permanent change has not occurred. Other promoting agents, such as the surfactants, cause a relatively permanent change in permeability, which is only overcome by turnover of the mucosal cells, a process which may require days for completion. Another potential advantage of the choline esters is that, unlike chelating agent such as EDTA, the choline esters may not necessarily sequester divalent cations (Mg++ or Ca++) which are necessary for the normal functioning of cells. In other words, there is no tissue damage at concentrations of choline esters which significantly increase drug absorption. In contrast to this, studies have indicated that surfactant activity, as with sodium lauryl sulfate, is generally associated with some degree of cellular damage. This lack of tissue damage affords a significant advantage to the use of choline esters in promoting drug absorption across mucosal cells. An added advantage is that they can be metabolized through normal pathways in the body. Thus, on enzymatic hydrolysis the choline esters produce choline and a fatty acid, both of which are normal endogenous components and nutritive agents. This eliminates a potential problem from introducing substances which are not normally present in the biochemical pathways of the body (e.g. salicylates, EDTA, etc.).

SUMMARY OF THE INVENTION

It has been found that when poorly absorbed drugs are administered in the nasal, buccal, sublingual and vaginal cavities, the bioavailability of said drugs is increased by administering together with a choline ester absorption enhancing agent.

Accordingly, it is an object of this invention to enhance the bioavailability of poorly absorbed drugs administered in the nasal, buccal, sublingual or vaginal cavities by administering therewith a choline ester absorption enhancing agent.

It is an object of the invention to provide a new dosage form utilizing a class of choline esters which when administered in the nasal, buccal, sublingual or vaginal cavities will provide an increased blood level of the therapeutic agent.

Another object of the invention is to provide a choline ester absorption promoter of mucous membrane drug absorption at concentrations which do not alter the normal morphology of the mucosal cells.

Still another object of the invention is to provide a choline ester series of absorption agents that are endogenous and can be metabolized through normal pathways available in the body.

Other objects, features and advantages of the invention will be apparent to those skilled in the art from the detailed description of the invention which follows.

All of the foregoing objects are readily attained by providing a method and drug form wherein the absorption of poorly absorbed drugs from the nasal, buccal, sublingual and vaginal cavities is enhanced. The method comprises the steps of preparing a dosage form suitable for nasal, buccal, sublingual or vaginal delivery, said dosage form comprising an effective unit dosage amount of the poorly absorbed drug, a choline ester absorption-enhancing agent or pharmaceutically acceptable salt thereof, the agent being present in said dosage form in an amount sufficient to be effective in enhancing the rate of the mucosal membrane absorption of the therapeutic agent, and pharmaceutically acceptable excipients.

DETAILED DESCRIPTION OF THE INVENTION

The present invention generally comprises the steps of preparing a dosage form capable of being administered in the nasal, buccal, sublingual or vaginal cavities, wherein the dosage form comprises an effective unit dosage amount of a poorly absorbed drug and a choline ester absorption enhancing agent, the choline ester being present in the dosage form in a sufficient quantity to be effective in enhancing mucous membrane absorption rates and administering the dosage form to warm-blooded animals. The amount of poorly absorbed drug varies over a wide range, but generally the thermapeutically effective unit dosage amount of the selected poorly absorbed drug depends on that amount known in the art to obtain the desired results.

The compounds that are used as absorption enhancers in our method and drug forms are fatty acid esters of choline and pharmaceutically acceptable salts thereof, of the formula:

$$[(CH_3)_3N^+CH_2CH_2OR]X^-$$

wherein R is:

(a) $C_2$—$C_{20}$ saturated acyl such as hexanoyl, octanoyl, decanoyl, lauroyl, myristoyl, palmitoyl, stearoyl and the like;

(b) $C_2$—$C_{20}$ acyl with 1 to 6 double bonds such as 2-hexenoyl, 9-decenoyl, 9-hexadecenoyl (palmitoleoyl), oleoyl, myristoleoyl, 9,12-hexadecadienoyl, α-linoleoyl, γ-linolenoyl, arachidyl and the like;

(c) $C_2$—$C_{20}$ hydroxyacyl with 1 to 3 hydroxy groups such as 2-hydroxylauroyl, 2-hydroxymyristoyl, 2-hydroxypalmitoyl and the like;

(d) $C_4$—$C_{20}$ ketoacyl such as 6-ketodecanoyl, 4-keto-9,11,13-octadecatrienoyl and the like;

(e) $C_5$—$C_{20}$ unsaturated hydroxyacyl such as 2-hydroxy-12-octadecenoyl and the like;

(f) $C_5$—$C_{20}$ carbalkoxyacyl such as ω-ethoxycarbonyloctanoyl and the like;

(g) arylacyl ($C_7$—$C_{20}$) such as phenylacetyl and the like;

(h) alkylaroyl ($C_7$—$C_{20}$) such as butylbenzoyl and the like;

(i) carboxyacyl ($C_5$—$C_{20}$) such as sebacyl; and X is a pharmaceutically acceptable counterion such as chloride, sulfate, nitrate, perchlorate, bromide, iodide phosphate, acetate, benzoate, tartrate, citrate, propionate, gluconate, lactate, maleate, fumarate, bezylate, camsylate, esylate, gluceptate, mesylate, napsylate and the like.

The preferred mucous membrane absorption enhancing agents of the above formula are:
1. hexanoylcholine
2. lauroylcholine
3. octanoylcholine
4. decanoylcholine
5. myristoylcholine
6. palmitoylcholine
7. stearoylcholine
8. 2-hexenoylcholine
9. 9-decenoylcholine
10. 9-hexadecenoylcholine
11. α-lineoylcholine
12. 2-hydroxylauroylcholine
13. 6-ketodecanoylcholine
14. ω-ethoxycarbonyloctanoylcholine
15. 2-hydroxypalmitoylcholine The most preferred absorption enhancing agents useful in our method and dosage forms are:
1. hexanoylcholine
2. octanoylcholine
3. decanoylcholine
4. lauroylcholine
5. myristoylcholine
6. palmitoylcholine
7. stearoylcholine
8. decanoylcholine and pharmaceutically acceptable salts of the above.

The choline ester absorption enhancing agents employed in the practice of this invention are known compounds which are commercially available and processes for their preparation are disclosed throughout the art.

Various active agents provide beneficial effects when administered to patients. Such agents which can be made more useful by enhancing their absorption in accordance with this invention, are exemplified by, but not limited to, the following classes of drugs:

(1) β-lactam antibiotics such as cefoxitin, N-formamidinylthienamycin, amoxicillin, ampicillin, azlocillin, bacampicillin, carbenicillin, cefaclor, cefadroxil, cefamandole, cefatrizine, cefazoline, cefonicid, cefaperazone, ceforanide, cefotaxime, cefotiam, cefroxadine, cefsulodin, ceftazidime, ceftizoxime, cephalexin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G., penicillin V., pivampicillin, piperacillin, pirbenicillin and the like.

(2) Aminoglycoside antibiotics such as gentamicin, amikacin, astromicin, betamicin, butikacin, butirosin, clindamycin, josamycin, kanamycin, neomycin, netilmicin, tobramycin and the like.

(3) Antiviral agentssuch as ara C (cytarabine), acyclovir, floxuridine, ribavirin, vidarabine, idoxuridine, trifluridine and the like.

(4) Amino acids such as methyldopa, carbidopa, levodopa, fludalanine, γ-aminobutyric acid and the like.

(5) Smooth muscle relaxants such as theophylline, aminophylline, diphylline, oxtriphylline, ambuphylline, fenethylline, guathylline, pentoxyfylline, xanthinol niacinate, theophylline glycinate, glucophylline and the like.

(6) Polypeptides such as cyclo(N-Me-Ala-Tyr-D-Trp-Lys-Val-Phe)acetate (L-363,586), somatostatin, insulin, gastrin, caerulein, cholecystokinin, atrial natriuretic factor, and the like.

(7) Anti-inflammatory agents such as indomethacin, sulindac, ibuprofen and the like.

(8) Diuretics such as aldactone, hydrochlorothiazide, amiloride, chlorothiazide, furosemide and the like.

The enhancement of drug absorption in accordance with this invention is not by any means limited to the above drugs, but are in general applicable to other classes of drugs such as analgesics, anabolics, androgens, anorexics, adrenergics, antiadrenergics, antiallergics, anti-bacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radionuclide diagnostic agents and the like.

Generally, the amount of adjuvant employed in the practice of the invention ranges from 0.05–500 mg in each dose. The percentage of adjuvant in the total combination of drug plus adjuvant is 0.05–50% with a preferred ratio of adjuvant in the total combination of adjuvant plus drug being 0.05–25%.

For nasal administration, the formulations may be prepared as drops, sprays, mists, aerosols, gels, and other standard procedures known in the art. The preferred formulation is a liquid drop composed of a minimum of 1 mg choline ester with the pharmacologically required dose of drug and sufficient excipients to formulate an acceptable composition. For oral application, the formulations may be prepared as gels, suspensions, polymers, tablets, and other standard procedures known in the art. The preferred formulation is a compressed tablet composed of a minimum of 1 mg choline ester with the pharmacologically required dose of drug and sufficient excipients to formulate an acceptable composition. For vaginal administration, the formulations may be prepared as solutions, suspensions, gels, suppositories, tablets, and other standard procedures known in the art. The preferred formulation is a solid suppository composed of a minimum of 1 mg choline ester with the pharmacologically required dose of drug and sufficient suppository base to formulate an acceptable composition. The methods and choice of excipients and suppository bases are well known to those skilled in the art and the composition of said formulations is not limited to liquid drops, compressed tablets or solid suppositories by this invention.

The following examples illustrate preparation of various compositions of the invention. The examples should be construed as illustrations rather than limitations thereof.

EXAMPLE 1

Effect of palmitoylcholine iodide on the nasal, buccal and vaginal absorption of α-methyldopa (amino acid, antihypertensive). Experiments were performed with rats wherein each animal received an aqueous formulation administered to the nasal, oral or vaginal cavities. The formulations contained the indicated amount of α-methyldopa in the presence or absence of 1.0 mg palmitoylcholine iodide. Procedures were tested to eliminate the possibility of cross-contamination between the nasal and oral cavities. Blood levels of α-methyldopa were determined by high performance liquid chromatography and the amount of drug absorbed (percent bioavailability) calculated against intravenous α-methyldopa administration.

| Administration Route | Dose of α-methyldopa (mg) | Percent α-methyldopa Bioavailability in the Absence (−) or Presence (+) of Palmitoylcholine* | |
|---|---|---|---|
| | | (−) | (+) |
| Nasal Cavity | 0.5 | 7 ± 1.1 | 86 ± 16.3 |
| Oral Cavity | 2.5 | 3 ± 0.7 | 5 ± 0.5 |
| Vaginal Cavity | 2.5 | 2 ± 1.0 | 55 ± 2.0 |

*Values represent the mean ± SD for n = 3 determinations.

EXAMPLE 2

Effect of palmitoylcholine iodide on the nasal, buccal and vaginal absorption of cefoxitin (β-lactam antibiotic). Experiments were performed with rats wherein each animal received an aqueous formulation administered to the nasal, oral or vaginal cavities. The formulations contained 2.5 mg sodium cefoxitin in the presence or absence of 1.0 mg palmitoylcholine iodide. Procedures were tested to eliminate the possibility of cross-contamination between the nasal and oral cavities. Blood levels of cefoxitin were determined by high performance liquid chromatography and the amount of drug absorbed (percent bioavailability) calculated against intravenous cefoxitin administration.

| Administration Route | Percent cefoxitin Bioavailability in the Absence (−) or Presence (+) of Palmitoylcholine* | |
|---|---|---|
| | (−) | (+) |
| Nasal Cavity | 15 ± 9.3 | 67 ± 17 |
| Oral Cavity | 0.4 ± 0.6 | 0.3 ± 0.5 |
| Vaginal Cavity | 2 ± 3.8 | 38 ± 3.1 |

*Values represent the mean ± SD for n = 3 determinations.

What is claimed is:

1. A pharmaceutical composition for enhancing absorption from the nasal, buccal, sublingual or vaginal cavities comprising a therapeutically effective dosage amount of an amino acid selected from the group consisting of methyldopa, carbidopa, levodopa, fludalanine and α-aminobutyric acid or a polypeptide selected from the group consisting of cyclo(N-Me-Ala-Tyr-D-Trp-Lys-Val-Phe) acetate, somatostatin, insulin, gastrin, caerulein, cholecystokinin and atrial natriuretic factors and a choline ester absorption enhancing agent of the formula:

$$[(CH_3)_3N^+CH_2CH_2OR]X^-$$

wherein R is saturated acyl ($C_2$—$C_{20}$), acyl($C_2$—$C_{20}$ with 1 to 6 double bonds, hydroxyacyl ($C_2$—$C_{20}$) with 1 to 3 hydroxy groups, ketoacyl ($C_4$—$C_{20}$), unsaturated hydroxyacyl ($C_5$—$C_{20}$), carboxyacyl ($C_4$—$C_{20}$), arylacyl ($C_7$—$C_{20}$) alkylaroyl ($C_7$—$C_{20}$) or carbalkoxyacyl ($C_5$—$C_{20}$) and X is a pharmaceutically acceptable counterion.

2. The composition of claim 1, wherein said amino acid is methyldopa, carbidopa or levodopa and said polypeptide is cyclo(N-Me-Ala-Tyr-D-Trp-Lys-Val-Phe) acetate, somatostatin, insulin or atrial natriretic factor and the choline ester absorption enhancing agent is selected from the group consisting of hexanoylcholine, decanoylcholine, lauroylcholine, octanoylcholine, myristoylcholine, palmitoylcholine, stearoylcholine, 2-hexenoylcholine, 9-decenoylcholine 9-hexadecenoylcholine, α-lineoylcholine, 2-hydroxylauroylcholine, 2-hydroxymyristoylcholine, 6-ketodecanoylcholine, 12-hydroxy-12-octadecanoylcholine, ω-ethoxycarbonyloctanoylcholine and 2-hydroxypalmitoylcholine.

3. The composition of claim 2, wherein said amino acid is methyldopa or levodopa and said polypeptide is cyclo(N-Me-Ala-Tyr-Lys-Val-Phe) acetate, atrial natriuetic factor, insulin or somatostatin and said enhancing agent is lauroylcholine, myristoylcholine, stearoylcholine or palmitolycholine.

4. The composition of claim 3, wherein said amino acid is methyldopa and said polypeptide is insulin said enhancing agent is palmitoylcholine.

5. The composition of claim 4, wherein said amino acid is α-methyldopa.

6. A method of enhancing the rate of absorption of an amino acid drug selected from the group consisting of methyldopa, carbidopa, levodopa, fludalanine and Y-aminobutyric acid or a polypeptide drug selected from the group consisting of cyclo(N-Me-Ala-Tyr-D-Trp- Lys-Val-Phe) acetate, somatostatin, insulin, gastrin, caerulein, cholecystokinin and atrial natriuretic factors administered to the nasal, buccal, sublingual or vaginal cavities, which comprises administering a composition comprising a therapeutically effective dosage amount of said drug and a choline ester absorption enhancing agent of the formula:

$$[(CH_3)_3N^+CH_2CH_2OR]X^-$$

wherein R is saturated acyl ($C_2$—$C_{20}$), acyl ($C_2$—$C_{20}$) with 1 to 6 double bonds, hydroxyacyl ($C_2$—$C_{20}$) with 1 to 3 hydroxy groups, ketoacyl ($C_4$—$C_{20}$), unsaturated hydroxyacyl ($C_5$—$C_{20}$), carboxyacyl ($C_4$—$C_{20}$) arylacyl ($C_7$—$C_{20}$), alkylaroyl ($C_7$—$C_{20}$) or carbalkoxyacyl ($C_5$—$C_{20}$) and X is a pharmaceutically acceptable counterion.

7. The method of claim 6, wherein said amino acid is methyldopa, carbidopa or levodopa and said polypeptide is cyclo(N-Me-Ala-Tyr-D-Trp-Lys-Val-Phe) acetate, somatostatin, insulin or atrial natriuretic factor and said choline ester absorption enhancing agent is selected from the group consisting of hexanoylcholine, decanoylcholine, lauroylcholine, octanoylcholine, myristoylcholine, palmitoylcholine, stearoylcholine, 2-hexenoylcholine, 9-decenoylcholine, 9-hexadecenoylcholine, α-lineoylcholine, 2-hydroxylauroylcholine, 2-hydroxymyristoylcholine, 6-ketodecanoylcholine, 12-hydroxy-12-octadecanoylcholine, ω-ethoxycarbonyloctanoylcholine and 2-hydroxypalmitoylcholine.

8. The method of claim 7, wherein said polypeptide is cyclo(N-Me-Ala-Tyr-D-Trp-Lys-Val-Phe) acetate somatostatin, or atrial natriuretic factor and the enhancing agent is hexanoylcholine, octanoylcholine, decanoylcholine, lauroylcholine, myristoylcholine, palmitoylcholine or stearoylcholine.

9. The method of claim 8, wherein said enhancing agent is palmitoylcholine.

10. The composition of claim 1 further comprising pharmaceutically acceptable excipients.

11. The method of claim 8, wherein the enhancing agent is palmitoylcholine.

12. The method of claim 7, wherein the amino acid ismethyldopa or levodopa and the enhancing agent is palmitoylcholine.

13. The method of claim 12, wherein the amino acid is α-methyldopa.

14. The method of claim 9, wherein the popypeptide is cyclo(N-Me-Ala-Tyr-D-Trp-Lys-Val-Phe) acetate.

15. The method of claim 9, wherein the polypeptide is atrial natriuretic factor.

* * * * *